(12) United States Patent
Spahn

(10) Patent No.: US 7,474,731 B2
(45) Date of Patent: Jan. 6, 2009

(54) SYSTEMS AND METHODS FOR ADAPTIVE IMAGE PROCESSING USING ACQUISITION DATA AND CALIBRATION/MODEL DATA

(75) Inventor: Martin Spahn, Chicago, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 292 days.

(21) Appl. No.: 11/546,742

(22) Filed: Oct. 12, 2006

(65) Prior Publication Data

US 2008/0056445 A1    Mar. 6, 2008

Related U.S. Application Data

(60) Provisional application No. 60/840,771, filed on Aug. 29, 2006.

(51) Int. Cl.
G01N 23/04 (2006.01)
G01D 18/00 (2006.01)

(52) U.S. Cl. .......................................... 378/62; 378/207

(58) Field of Classification Search ................ 378/4, 378/19, 62, 98.8, 108, 207, 16; 382/128, 382/132, 284, 294
See application file for complete search history.

(56) References Cited

U.S. PATENT DOCUMENTS

| | | | |
|---|---|---|---|
| 5,962,856 A | 10/1999 | Zhao et al. | |
| 6,094,474 A * | 7/2000 | Vezina | ........................ 378/156 |
| 6,222,901 B1 | 4/2001 | Meulenbrugge et al. | |
| 6,655,836 B2 | 12/2003 | Boehm et al. | |
| 6,707,881 B2 | 3/2004 | Boehm et al. | |
| 6,718,011 B2 | 4/2004 | Spahn | |
| 6,859,521 B2 | 2/2005 | Spahn | |
| 6,912,266 B2 | 6/2005 | Spahn | |
| 6,978,051 B2 * | 12/2005 | Edwards | ....................... 382/284 |
| 7,075,061 B2 | 7/2006 | Spahn | |
| 7,086,779 B2 | 8/2006 | Fadler | |

(Continued)

FOREIGN PATENT DOCUMENTS

DE    3641992 A1    6/1988

(Continued)

OTHER PUBLICATIONS

"Adaptive Spatial-temporal filtering applied to x-ray fluoroscopy angiography" by Gert Schoonenberg, et al.

(Continued)

*Primary Examiner*—Irakli Kiknadze
(74) *Attorney, Agent, or Firm*—Alexander J. Burke; Peter L. Kendall

(57) ABSTRACT

A system and method in which image processing parameters that are used globally or which change locally within the image are adapted to improve image quality by using the acquisition parameters, image analysis data, and calibration/model data. Image processing parameters are established as a function of the acquisition parameters. The acquisition parameters include one or more of an x-ray tube voltage, a pre-filtration, a focal spot size, an x-ray source to detector distance (SID), and a detector readout mode. Image processing parameters may also be established as a function of local or global image analysis, such as signal-to-noise ratio, as well as a function of predicted signal-to-noise ratio determined from the calibration data and a predetermined model.

28 Claims, 5 Drawing Sheets

U.S. PATENT DOCUMENTS

| | | | |
|---|---|---|---|
| 7,099,430 | B2 | 8/2006 | Muller |
| 2005/0161610 | A1 | 7/2005 | Spahn |
| 2006/0182322 | A1* | 8/2006 | Bernhardt et al. ........... 382/128 |
| 2006/0188063 | A1 | 8/2006 | Spahn |

FOREIGN PATENT DOCUMENTS

| DE | 10201321 A1 | 7/2003 |
|---|---|---|

OTHER PUBLICATIONS

"Motion Detection Algorithms" by Andrew Kirillov; posted Apr. 30, 2005.

"A quantitative comparison of motion detection algorithms in fMRi" by Babak A. Ardekani, et al.; received Apr. 11, 2001; accepted Jun. 17, 2001.

"Retrospective Motion Correction in Digital Subtraction Angiography: A Review" by Erik H. W. Meijering, et al.; IEEE Transactions on Medical Imaging, vol. 18, No. 1, Jan. 1999, pp. 2-21.

"Motion Detection for Adaptive Spatio-Temporal Filtering of Medical X-Ray Image Sequences" by Marc Hensel, et al.; 2005 Springer. In: H.-P. Meinzer, et al. (Edt.): *Bildverarbeitung für die Medizin 2005: Algorithmen, Systems, Anwendungen*, Springer, 2005 (ISBN 3-540-25052-2). Proceedings BVM 2005, Heidelberg, Germany, Mar. 13-15, 2005.

"A 3-D space-time motion detection for an invariant image registration approach in dig angiography" vol. 97, Issue 1 (Jan. 2005).

"Evaluating Motion Detection Algorithms: Issues and Results" by J. Renno, et al.

"Motion Detection and Recognition Research" by Randal C. Nelsonand, et al.

"A Robust and Computationally efficient motion detection algorithm based on background estimation" by A. Manzenera, et al.

Chaper 10. "Controlling Frame Rate" Part II. Programming with OpenGL Performer.

\* cited by examiner

SYSTEMS AND METHODS FOR ADAPTIVE IMAGE PROCESSING USING ACQUISITION DATA AND CALIBRATION/MODEL DATA

CROSS-REFERENCE TO RELATED APPLICATIONS

This application claims a priority benefit to provisional application Ser. No. 60/840,771, filed on Aug. 29, 2006 and entitled "Adaptive Image Processing Using Actual X-ray Acquisition Data and Predetermined Calibration Data," which is hereby incorporated by reference in its entirety herein.

BACKGROUND

1. Field of the Invention

This invention relates generally to imaging systems, and in particular to cardiac and peripheral angiographic imaging. In particular, the present invention is directed to a system and method of using x-ray acquisition data, image analysis data, and calibration/model data to perform image processing.

2. Background Discussion

Radiography is the use of certain spectra of electromagnetic radiation, usually x-rays, to image a human body. Angiography, a particular radiographic method, is the study of blood vessels using x-rays. An angiogram uses a radiopaque substance, or contrast medium, to make the blood vessels visible under x-ray. Angiography is used to detect abnormalities, including narrowing (stenosis) or blockages (occlusions), in the blood vessels throughout the circulatory system and in certain organs.

Cardiac angiography, also known as coronary angiography, is a type of angiographic procedure in which the contrast medium is injected into one of the arteries of the heart, in order to view blood flow through the heart, and to detect obstruction in the coronary arteries, which can lead to a heart attack.

Peripheral angiography, in contrast, is an examination of the peripheral arteries in the body; that is, arteries other than the coronary arteries. The peripheral arteries typically supply blood to the brain, the kidneys, and the legs. Peripheral angiograms are most often performed in order to examine the arteries which supply blood to the head and neck, or the abdomen and legs.

Unfortunately, the conditions of image acquisition for x-ray imaging in medical diagnostic or interventional procedures can vary strongly from patient to patient due to weight, constitution, age, and other factors. The conditions may also vary from procedure to procedure due to different angulations, x-ray source to detector distances, and other factors. The conditions may also vary from operator to operator due to personal preferences or skills.

Thus, conventional imaging techniques that generate images under different conditions result in images that often vary quite substantially and may require different image processing parameters to generate optimal final images. This drawback applies to single x-ray images as well as sequences of x-ray images.

Therefore, it would be an advancement in the state of the art to utilize acquisition data and calibration/model data together with image processing to enhance the quality of image data generated under different conditions.

SUMMARY

In view of the foregoing, the present invention is directed to a system and method for adaptive image processing that utilizes information such as acquisition data, image analysis data, such as signal-to-noise levels, and calibration/model data to direct image processing.

Accordingly, one embodiment of the present invention is directed to a method for establishing image processing parameters. The method includes accessing acquisition parameters for image data. Image processing parameters are established as a function of the acquisition parameters. (Acquisition parameters relate to the parameters and other information related to the conditions of the x-ray detector at the time a particular image was acquired.) The acquisition parameters include one or more of an x-ray tube voltage, a pre-filtration, a focal spot size, an x-ray source to detector distance (SID), and a detector readout mode.

Another embodiment is directed to the above-described method (hereinafter, "the method") that also includes determining a signal level and a noise level of the image data. Image processing parameters are established as a function of the acquisition parameters and the signal level and the noise level of the image data.

Yet another embodiment is directed to the method and also includes identifying one or more regions of the image data and determining a signal level and a noise level of each region. Global image processing parameters are established as a function of the acquisition parameters. Local image processing parameters are determined for each region as a function of the signal level and the noise level of each region.

Yet another embodiment is directed to the method and also includes accessing calibration data and identifying an expected signal level and an expected noise level of the image data as a function of a predetermined model of the acquisition parameters and the calibration data. The expected signal level and the expected noise level are utilized in the step of establishing image processing parameters. Calibration data relates to expected image analysis properties (such as signal-to-noise ratio) of an output image acquired from a detector operating under certain conditions (acquisition parameters). The predetermined model relates to a set of mathematic expressions and logical rules that express the relationship of certain properties (such as signal-to-noise ratio) of the output image to the acquisition data and calibration data. That is, a model predicts properties of the output image as a predetermined function of acquisition data and calibration data.

Yet another embodiment is directed to a method for identifying image processing parameters. The method includes accessing image data and accessing acquisition parameters for the image data. An average signal level and an average noise level of the image data are determined and regions of the image data are identified. A signal level and a noise level of each region is determined. Global image processing parameters are established as a function of the acquisition parameters and the average signal level and the average noise level of the image data. Local image processing parameters are established for each region as a function of the signal level and the noise level of each region.

Yet another embodiment is directed to a method for identifying image processing parameters wherein the acquisition parameters include an x-ray tube voltage and a detector readout mode.

Yet another embodiment is directed to a method for identifying image processing parameters wherein the detector readout mode comprises one or more of a zoom size and a binning size.

Yet another embodiment is directed to a method for identifying image processing parameters wherein the global image processing parameters include a kernel size and a gain of a dynamic range compression algorithm.

Yet another embodiment is directed to a method for identifying image processing parameters wherein the local image processing parameters include a kernel size and a gain of an edge enhancement algorithm.

Yet another embodiment is directed to a method for identifying image processing parameters and also includes accessing calibration data, and identifying an expected signal level and an expected noise level of the image data as a function of a predetermined model of the acquisition parameters and the calibration data. The expected signal level and the expected noise level are utilized in the step of identifying global image processing parameters.

Yet another embodiment is directed to a method for selecting image processing parameters. The method includes receiving image data and measuring an average signal level and an average noise level of the image data. The image data is divided into a plurality of regions of interest and a signal level and a noise level of each region of interest are measured. Global image processing parameters are selected as a function of the average signal level and the average noise level of the image data. Local image processing parameters are selected for each region of interest as a function of the signal level and the noise level of each region.

Other embodiments of the present invention include the methods described above implemented using apparatus or programmed as computer code to be executed by one or more processors operating in conjunction with one or more electronic storage media. As one of ordinary skill in the art would readily appreciate, the same features and modifications described above with regard to the method can be equally applied to an apparatus and a system.

BRIEF DESCRIPTION OF THE DRAWINGS

To the accomplishment of the foregoing and related ends, certain illustrative aspects of the invention are described herein in connection with the following description and the appended drawings. These aspects are indicative, however, of but a few of the various ways in which the principles of the invention may be employed and the present invention is intended to include all such aspects and their equivalents. Other advantages and novel features of the invention may become apparent from the following description of the invention when considered in conjunction with the drawings. The following description, given by way of example, but not intended to limit the invention solely to the specific embodiments described, may best be understood in conjunction with the accompanying drawings, in which.

DETAILED DESCRIPTION

Figure 1:
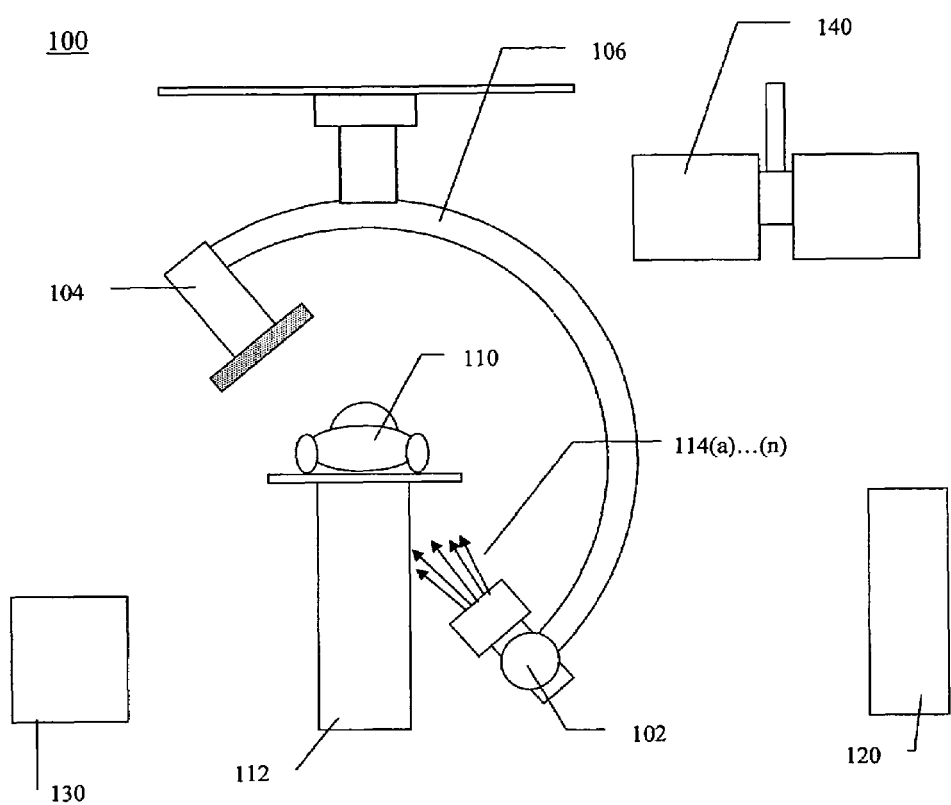
FIG. 1 shows an x-ray imaging system for which the globally and/or locally varying image processing parameters may be adjusted.

It is noted that in this disclosure and particularly in the claims and/or paragraphs, terms such as "comprises," "comprised," "comprising," and the like can have the meaning attributed to it in U.S. patent law; that is, they can mean "includes," "included," "including," and the like, and allow for elements not explicitly recited. Terms such as "consisting essentially of" and "consists essentially of" have the meaning ascribed to them in U.S. patent law; that is, they allow for elements not explicitly recited, but exclude elements that are found in the prior art or that affect a basic or novel characteristic of the invention. As used in this application, the terms "component" and "system" are intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed between two or more computers. These and other embodiments are disclosed or are apparent from, and encompassed by, the following description.

A detailed description of radiography, angiography, and x-ray imaging systems may be found in the following treatises:

Baum, Stanley and Michael J. Pentecost, eds. *Abram's Angiography*, 4$^{th}$ ed. Philadelphia: Lippincott-Raven, 1996, which is hereby incorporated by reference in its entirety herein;

Jeanne, LaBergem, ed. *Interventional Radiology Essentials*, 1$^{st}$ ed. Philadelphia: Lippincott Williams & Wilkins, 2000, which is hereby incorporated by reference in its entirety herein; and Johns, Harold E. and John R. Cunningham. *Physics of Radiology*, 4$^{th}$ ed. Charles C. Thomas Publisher Ltd., 1983, which is hereby incorporated by reference in its entirety herein.

Conventional imaging techniques that generate images under different conditions result in images that often vary quite substantially and may require different image processing parameters to generate optimal final images. Conditions of x-ray image acquisition may vary based on the particular application being performed and the particular system being used. For example:

Radiographic systems are usually used to acquire individual exposures, and typical applications include thoracic and skeletal imaging.

Fluoroscopic systems are primarily used for the imaging of dynamic processes but can also be used to acquire individual exposures. Typical applications of fluoroscopic systems include imaging the esophagus, stomach and colon, imaging a swallowing operation, examining the venous system using a contrast medium (phlebography), and imaging the spinal cord after the injection of a contrast agent (myelography).

Angiographic systems are usually dedicated systems for vascular imaging and intervention. Vascular procedures in angiography involve guiding catheters through the arterial or venous systems to permit the injection of contrast media and/or the attachment or detachment of interventional tools (stents, coils, etc.) at specific locations.

Cardiac systems are used for the diagnosis of cardiac diseases and for coronary intervention.

Multifunctional systems are designed to meet the requirements that apply to examinations in areas ranging from radiography and fluoroscopy to angiography.

In view of the foregoing, embodiments of the present invention include systems and methods in which image processing parameters that are used globally or which change locally within the image are adapted to improve image quality by using acquisition parameters, image analysis data, and calibration/model data. Image processing parameters are established as a function of the acquisition parameters. Acquisition parameters relate to the parameters and other information related to the conditions of the x-ray detector at the time a particular image was acquired. Examples of acquisition parameters include an x-ray tube voltage, a pre-filtration, a focal spot size, an x-ray source to detector distance (SID), a detector readout mode, a frame rate, and a pulse length.

The examples of acquisition parameters described here are illustrative only, and those of ordinary skill in the art will recognize that the present invention may be applied to other acquisition parameters not specifically identified here. Some examples of acquisition parameters to which the present invention could be applied include:

(1) X-ray spectral information, such as power (kV) and pre-filtration (typically Al or Cu filters that may be added or removed automatically from the x-ray tube collimator);

(2) Geometrical information, such as the SID (source to detector distance), and angulation (position of the C-arm with respect to the table);

(3) Generator current (mA), pulse length (s), and the product of generator current and pulse length (mAs);

(4) Dose information (measured close to the source in the x-ray collimator area); and (5) Detector mode parameters, such as pixel size, zoom size, binned or non-binned readout, amplification gain, etc.

According to an embodiment of the invention, illustrated in FIG. 1, a patient 110 is placed on a table 112. A support member, such as a C-arm, 106 supports an x-ray emitting unit, such as an x-ray tube, 102 and an x-ray detecting unit, such as an x-ray detector, 104. The x-ray emitting unit 102 is adapted to emit x-rays 114(a) ... (n) (identifying a plurality of x-ray signals), and the x-ray detecting unit 104 is adapted to absorb and measure the emitted x-rays. Images of all or parts of the patient 110 may be obtained using the x-ray emitter 102, x-ray detector 104, and x-rays 114. The images typically assist in the diagnosis and/or treatment of the patient 110.

A generator unit 120 is used to generate the x-rays emitted by the x-ray emitting unit 102. The x-ray generator 120 is typically, for example, an x-ray producing device that includes a source of electrons, a vacuum within which the electrons are accelerated, and an energy source that causes the electrons to be accelerated.

A system control unit and imaging system 130 controls the operation of the entire system 100, performs image processing, and transmits the image data for display on the image display unit 140. The display unit 140 is used to display the image data generated by the system 100. The display unit 140 may be, for example, a monitor, LCD (liquid crystal display), a plasma screen, or other module adapted to display output data typically by a representation of pixels. The system control and imagining system 130 includes a processor and memory modules and is described in relation to FIG. 2.

Figure 2:
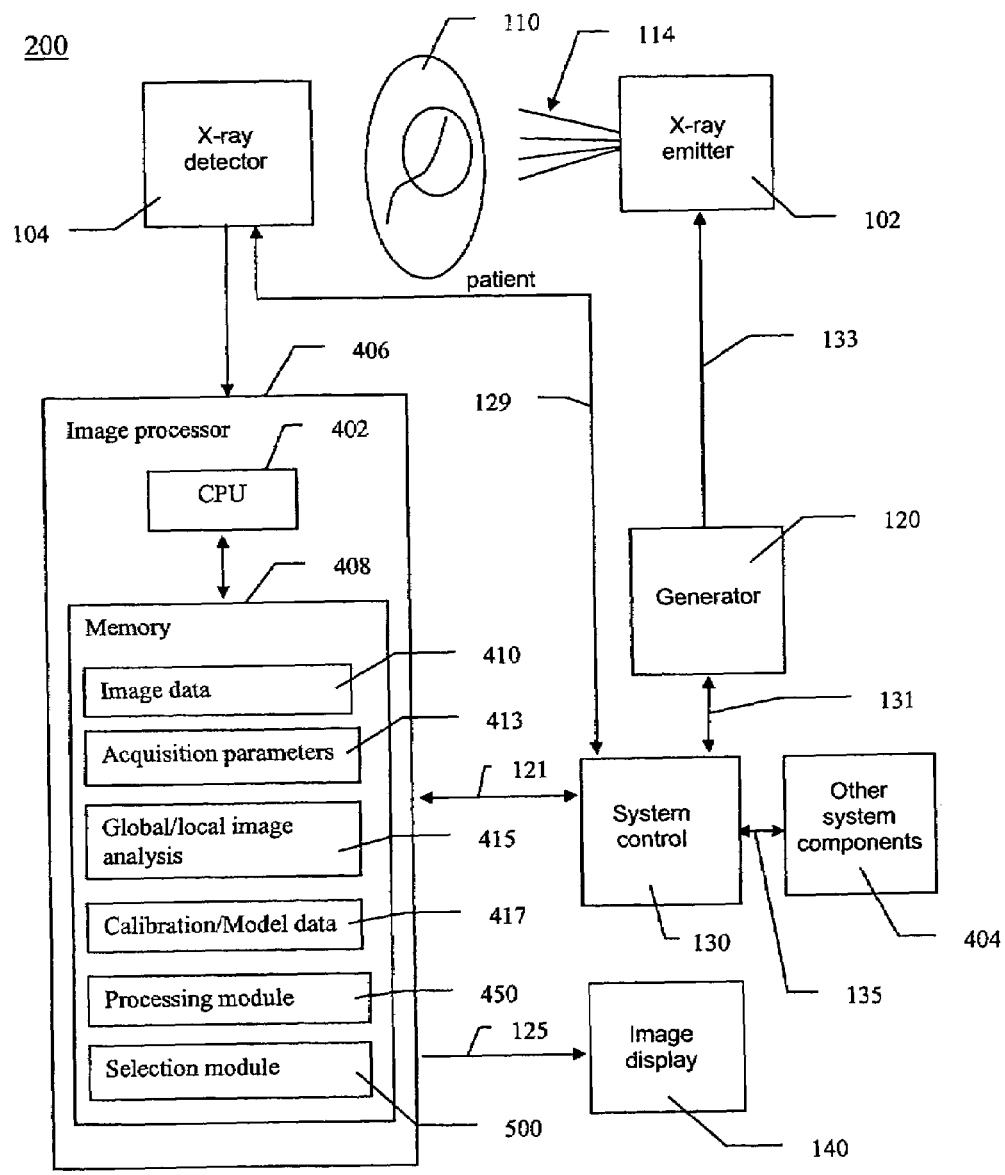
FIG. 2 illustrates a block diagram of an imaging system for which the globally and/or locally varying image processing parameters may be adjusted.

FIG. 2 is a diagram 200 showing selected components used in an adaptive image processing system and method. As shown in FIG. 2, x-rays 114 are emitted from an x-ray emitting unit, such as an x-ray tube, 102 and directed toward a patient 110. X-rays are detected by an x-ray detecting unit 104. The detected x-ray signals are transmitted, via transmission medium 127, which is typically a wire connection, communication bus, such as an IEEE bus, or other data transmission medium suitable to transmit data signals or pulses that represent the output from x-ray detector 104, to an image processing module 406. The image processing module 406 (described in more detail below) is in bi-directional communication, via transmission medium 121, which may be a wire, wireless, or communication bus or other transmission medium suitable to transmit data signals, with system control unit 130 (described in more detail below) and is in communication with image display unit 140, via transmission medium 125. The image processor 406 processes the acquired image data and provides the output to system control unit 130, which is in bi-directional communication, via transmission medium 135, with other system components 404.

The system control unit 130 provides control signals to generator unit 120, via transmission medium 131. The generator unit 120 adjusts, if necessary, the x-rays emitted by x-ray emitting unit 102, via control signals transmitted using transmission medium 133. The system control unit 130 provides control signals to x-ray detector 104, via transmission medium 129, which adjusts, if necessary, the detection of the emitted x-rays by the x-ray detecting unit 104.

The image processing module 406 includes a central processing unit (CPU) 402, which is in bi-directional communication with memory module 408.

The CPU 402 is typically a processor that includes an arithmetic logic unit (ALU), which performs arithmetic and logical operations, and a control unit (CU), which extracts instructions from memory and decodes and executes them, utilizing the ALU when necessary.

The memory module 408 includes image memory module 410, acquisition parameter storage module 413, global/local image analysis module 415, model data module 417, processing algorithm module 450, and selection algorithm module 500.

Image memory module, or facility, 410 is used to store image data either received from the x-ray detecting unit 104 or generated by the CPU 402 of the image processor 406 based on detected x-rays from x-ray detecting unit 104. This includes raw image data as well as image data that has undergone image processing. The image memory 410 is typically an electronic storage medium adapted to store received data in electronic form and may be solid state storage, such as random access memory (RAM) or cache memory. It may also include recorders to record to and read from mass storage devices such as, for example, optical disks, magnetic disks, flash semiconductor disks, and other types of storage which may be temporary or permanent. The image memory may be accessed such that the contents of the memory are provided to the CPU 402 and/or system controller 130. Once the data has been accessed, typically by program code to fetch, or retrieve, the desired data stored in memory, it may be processed to determine the one or more image processing parameters as described in greater detail below.

Acquisition parameter storage module, or facility, 413 includes information related to the acquisition of image data, such as x-ray tube voltage level, pre-filtration, focal spot size, x-ray source to detector distance (SID), and detector readout mode (e.g., zoom size, binned or unbinned pixels). The acquisition parameter storage module 413 includes electronic storage capabilities and stores the acquisition data, as well as provides the acquisition data to CPU 402, which can process the data.

Global/local image analysis module, or facility, 415 stores processing code to measure globally and locally varying image properties. Memory module 415 is also used to store (1) the globally measured signal and noise (e.g., average signal and average noise) that are used to adapt the globally operating image processing parameters (e.g., those which do not change due to local image content); and (2) the locally measured signal and noise that are used to adapt the locally operating image processing parameters (e.g., within certain regions of interest which coincide with the area within which a locally operating image algorithm operates, such as the kernel size of an edge enhancement algorithm).

Global parameters may include the kernel size and the gain of a dynamic range compression algorithm (partial subtraction of the low-passed image of a given kernel size). Local parameters may include the gain and the kernel size of an edge-enhancement algorithm which adapts to the local noise level or the local signal-to-noise ratio. The same concept may also be applied to spatial frequency domains. That is, image processing parameters operating in given spatial frequency bands (rather than spatial domains) may be adaptively established based on acquisition data. The global/local image analysis module 415 includes electronic storage capabilities and stores the data, as well as provides the data to CPU 402, which can process the data.

Various global and local image analysis parameters are within the scope of this invention, and the description, or listing, here is not intended to be either exhaustive or limiting. Some examples of global and local image analysis parameters include:

(1) Global signal level, global noise level, and global signal-to-noise ratio;

(2) Local signal level, local noise level, and local signal-to-noise ratio;

(3) Contrast (that is, local signal difference);

(4) Histogram width and distribution, including such derivative histogram properties as a 50% median value (both globally and locally within a given ROI); and (5) Spectral frequency distribution (both locally and globally).

Calibration/model data module, or facility, 417, stores calibration data and a predetermined model which are used to predict expected image analysis properties. The predicted image analysis properties are compared with measured image analysis data to be used in the image processing parameter adaptation. The model may predict global image analysis properties (average signal and average noise) as well as local image analysis properties, e.g., within certain ROIs (regions of interest) which coincide with the area within which a locally operating image algorithm operates (for example, the kernel size of an edge enhancement algorithm). The calibration/model data module 417 includes electronic storage capabilities and stores the calibration data, the predetermined model, as well as provides the calibration data and the predetermined model to CPU 402, which can process the calibration data and the predetermined model.

Calibration data relates to the typical image analysis properties (e.g., expected signal-to-noise ratio) for a given set of acquisition parameters of the x-ray detector used to acquire a particular image. Calibration data may include signal level, noise level, signal-to-noise ratio, and resolution measurements based on a selected set of conditions defined by the acquisition parameters. However, the calibration data described here is illustrative of only a few representative embodiments and is not meant to be an exhaustive or complete listing. Calibration data may provide, for example, the typical signal, noise, and signal-to-noise ratio for a given set of acquisition parameters (such as, kV, mAs, SID, and simulated patient thickness). (Patient thickness may be simulated with 30 cm of water or plexiglass equivalent.) That is, calibration data relates to expected image analysis properties (such as signal-to-noise ratio) for a given detector and readout mode for a given application. For example, low-dose fluoroscopic acquisitions will use a higher gain readout mode than a single high-dose acquisition. In another example, a binned or a non-binned readout will provide different signal and noise levels.

A predetermined model is a set of mathematic expressions and logical rules that define the operation of an x-ray detector under certain conditions (under certain acquisition parameters). The predetermined model defines the relationship between certain properties (such as signal-to-noise ratio) of the output data and the acquisition data and calibration data based on a predetermined set of equations. That is, a model allows the prediction of certain properties of the output data based on the acquisition data and the calibration data. For example, a model allows one to predict, or calculate, an expected signal, noise, and signal-to-noise level of an output image given the acquisition parameters and the calibration data of the x-ray detector that was used to acquire the output image. That is, a model predicts properties of the output data as a function of acquisition data and calibration data.

A model is not limited to the description here, and may be used to predict other properties of the output image. For example, the model may predict:

(1) Signal level, noise level, and signal-to-noise ratio;

(2) Spatial resolution, taking the focal spot size, the SID (source to detector distance), and the binning (or non-binning) of the detector into account;

(3) Effective patient thickness from the knowledge of the angulation, position of the table with respect to the tube and detector, the application (whether it is a cardiac, peripheral, or a neurological procedure), and a modeled average patient. The effective patient thickness is an estimate of the effective amount of penetrated tissue. An initial prediction of a small, medium, or large patient size may also be made from the acquisition parameters and/or the measured signal or noise. The remaining procedure could then utilize the prediction of patient size to improve the prediction of the signal level, noise level, signal-to-noise ratio, etc.; and (4) Absorption in the table or the x-ray scatter grid, taking the geometry (angulation, degree of defocussing, etc.) into account. Utilizing the absorption in the table or x-ray scatter grid could also be used to improve the prediction of the signal level, noise level, signal-to-noise ratio, etc.

The model may be used together with the knowledge of the calibration data to make predictions of image analysis parameters. Use of the calibration data together with a predetermined model allows for more precise predictions than the use of the model or the calibration data alone would allow.

Processing algorithm module 450 is typically an electronic storage medium that stores a processing algorithm, which is a series of steps to process, adjust, or modify the image data received from detector 104. The output of the processing algorithm module 450 is provided to the CPU 402. The processing algorithm module 450 is described in greater detail in relation to FIG. 4.

Selection algorithm module 500 is typically an electronic storage medium that stores a selection algorithm, which is a series of steps to adjust, or modify the image data received from detector 104. The output of the selection algorithm module 500 is provided to the CPU 402. The selection algorithm module 500 is described in greater detail in relation to FIG. 5.

The image processor 406 outputs an adjusted, or modified, image data after the image data has been processed via either processing algorithm module 450 or selection algorithm module 500. The output may be provided to image display module 140 and/or system control module 130, via transmission media 125 and/or 121, respectively.

The output from the image processing module 406 may be provided to image display module 140, via transmission medium 125. The image display module 140 is typically a monitor, LCD (liquid crystal display), a plasma screen, or other graphical user interface that can display output data. Also, the image display module 140 may be coupled to another CPU, processor, or computer, such as a desktop computer or a laptop computer (not shown) and may also be coupled to a keyboard, a mouse, a track ball, or other input device (not shown) to adjust the view, dimensions, color, font, or display characteristics of the image display module 140.

The image processing module 406 and/or image display module 140, may also be coupled to a printer (not shown) to print the output; or a transmission module, such as a DSL line (not shown) or a modem, such as a wireless modem (not shown), or the Internet, to transmit the output to a second location or another display module.

Figure 3:
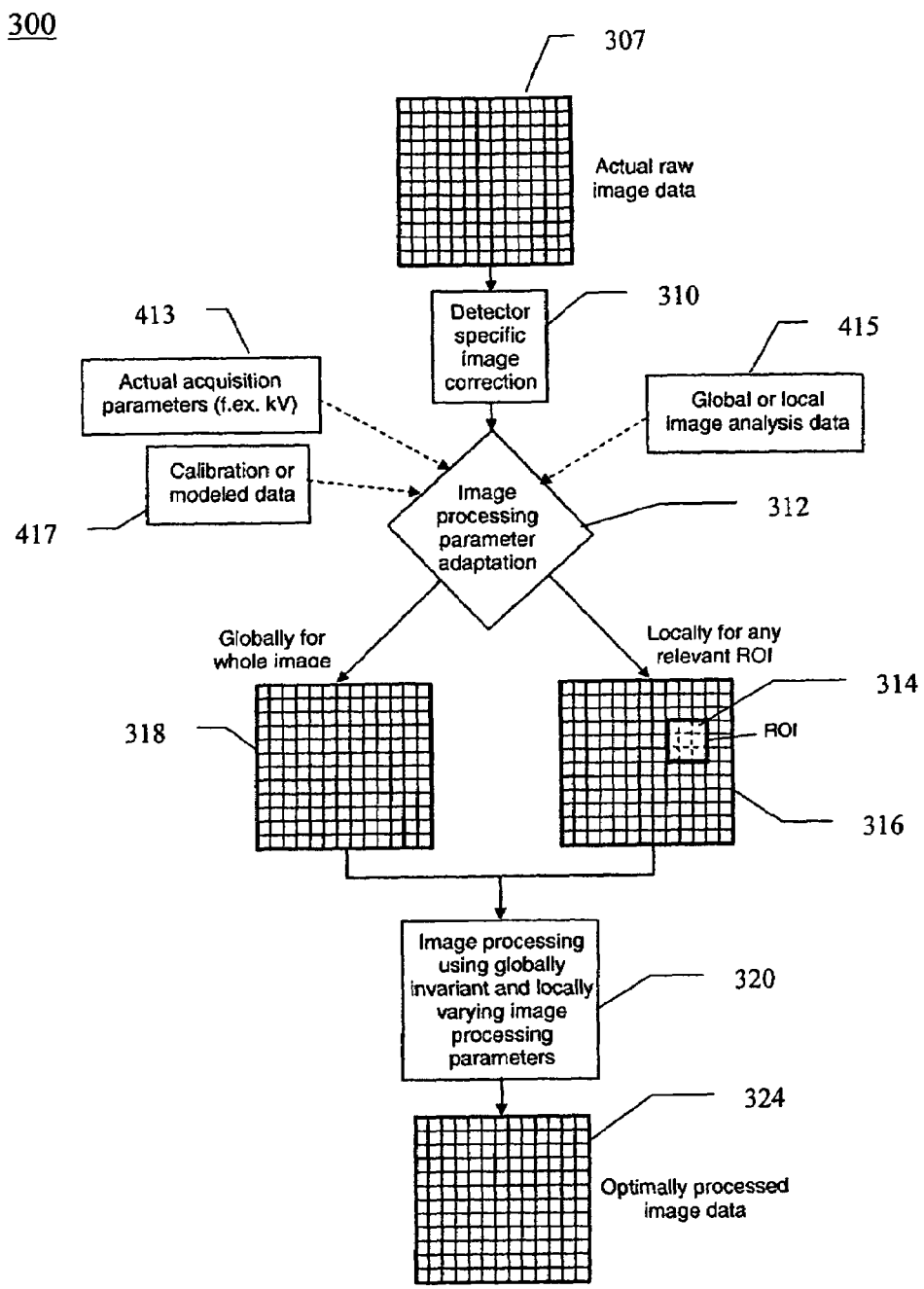
FIG. 3 shows an embodiment of an image pipeline with globally acting or locally varying image processing parameters.

FIG. 3 shows a diagram 300 of steps and image data, which may stored on, and/or retrieved from, an electronic medium. FIG. 3 shows an embodiment of an image pipeline with globally acting or locally varying image processing parameters which change due to (i) acquisition parameters used to acquire that image, (ii) image analysis data, and (iii) expected image analysis data determined based on the acquisition parameters, calibration data, and a predetermined model. In order to improve the image processing parameters used globally for the whole image or locally within certain areas of the image, the steps of FIG. 3 are illustrative of an embodiment of the present invention.

Actual image data is shown as 307. This image data is typically generated by an x-ray detector and stored in electronic memory. Detector-specific image correction processing is performed, as shown in step 310.

The acquisition parameters 413 for the actual image data are taken into account in the process 300. These parameters may include, for example, x-ray tube voltage, pre-filtration, focal spot size, x-ray source to detector distance (SID), and detector readout mode (zoom size, binned or unbinned pixels). However, these acquisition parameters are illustrative only and are not intended to limit the scope of the invention.

Step 415 shows that the average signal in the actual image and the average noise level in the actual image (global signal and noise) as well as local signal and local noise are measured.

The globally measured signal and noise (e.g., average signal and average noise) are used to adapt the globally operating image processing parameters (e.g., those which do not change due to local image content). The local signal and local noise are used to adapt the locally varying image processing parameters, e.g., within certain ROIs (regions of interest) which coincide with the area within which a locally operating image algorithm operates (for example, the kernel size of an edge enhancement algorithm).

Global parameters may include the kernel size and the gain of a dynamic range compression algorithm (partial subtraction of the low-passed image of a given kernel size). Local parameters may include the gain and the kernel size of an edge enhancement algorithm which adapts to the local noise level or the local signal-to-noise ratio. These examples of global and local image processing parameters are illustrative only and are not intended to limit the scope of the invention.

The same concept may be applied to the spatial frequency domain. That is, image processing parameters operating in given spatial frequency bands (rather than spatial domains) may be adaptively established based on acquisition data and calibration/model data.

Step 417 shows that calibration data, together with a predetermined model, are used to make a prediction of image analysis data, such as signal and noise values, for the image parameter adaptation. This is done globally (average signal and average noise) as well as locally, e.g., within certain ROIs (regions of interest) which coincide with the area within which a locally operating image algorithm operates (for example, the kernel size of an edge enhancement algorithm).

Image processing parameter adaptation is performed in step 312. Matrix 318 is a global matrix for the entire image and matrix 316 is divided into smaller regions of interest (ROIs), including ROI 314. Image processing, using globally invariant and locally varying image processing parameters, is performed as shown in step 320.

The optimally processed image data 324 is output.

The complexity of usage of acquisition parameters, image analysis data, and calibration/model data to drive globally used or locally varying image processing parameters may be escalated in the following ways:

In one implementation, only the acquisition parameters (such as x-ray voltage measured in kV) are taken into account to drive the image processing parameters. This will generally apply to globally acting image processing parameters.

In another implementation, image analysis data, both globally and locally in the image (such as signal and noise), are taken into account to drive global or locally varying image processing parameters.

In another implementation, both acquisition parameters and image analysis data are used to drive the global and locally varying image processing parameters.

In yet another implementation, acquisition parameters, global and local image analysis data, and calibration/model data are used to drive global and local image processing parameters.

Some examples of how image processing parameters may be adapted based on acquisition parameters, image analysis data, and calibration/model data, include the following. These examples are illustrative of but a wide range of configurations in which the present invention may be applied, and are not intended to limit the scope of the invention.

(1) The voltage of the x-ray detector used to acquire the current image data may be used to determine the global gain value of a dynamic range compression algorithm (for example, high gain values may be appropriate for low voltage, since the contrast differences are high; while lower gain values may be appropriate for high voltage, since the object penetration of high-voltage photons is less discriminating).

(2) The applied focal spot size during an x-ray acquisition sequence may be used to determine the value of parameters of sharpening algorithms (a large focal spot, which generates a blurrier image, may require higher edge enhancement settings to generate a sharper image than a smaller focus, which itself generates sharper images).

(3) The distance between source and object (table plus some assumed distance), and between object and detector may be used, in addition to the focal spot size, to determine the degree to which the parameters of sharpening algorithms may be altered.

(4) The locally measured noise, or signal-to-noise ratio, may be used to determine the gain of an edge enhancement algorithm.

(5) The locally measured noise, or signal-to-noise ratio, the applied power (measured in kV), and calibration data which, together with a predetermined model, predict the noise and signal-to-noise ratio for the applied power (measured kV) may be used to determine the locally varying gain of an edge enhancement algorithm.

Figure 4:
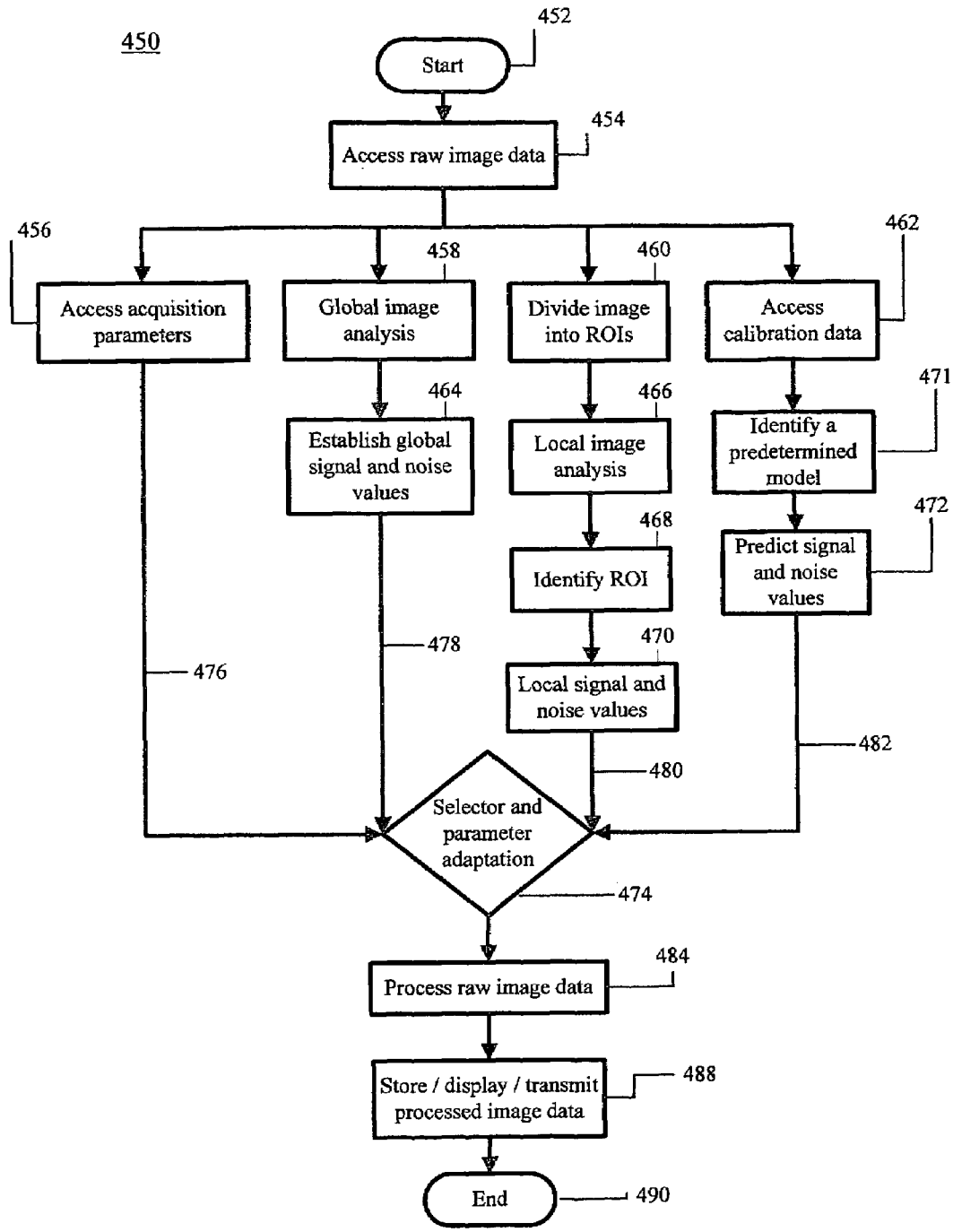
FIG. 4 is a flowchart of steps to implement an embodiment of the present invention.

FIG. 4 shows an algorithm 450 to process image data using acquisition parameters, image analysis data, and calibration/model data. The steps of FIG. 4 may be stored on a computer-readable medium, such as ROM, RAM, EEPROM, CD, DVD, or other non-volatile memory. Algorithm 450 may be retrieved, accessed, or downloaded from a remote location. Step 452 shows that the process begins.

Raw image data is accessed, as shown in step 454. This data is typically received from an x-ray detector. Step 456 shows that acquisition parameters are accessed and line 476 shows that acquisition parameter data is provided to selection step 474.

Global image analysis is performed, as shown in step 458. A global signal value and a global noise value are determined, as shown in step 464. These values are provided to selection step 474, via line 478.

The raw image data may be sub-divided into ROIs, as shown in step 460. Local image analysis may be performed as shown in step 466. ROIs are identified, as shown in step 468. Local signal, noise, and signal-to-noise values are established in step 470 and provided to selection step 474, via line 480.

Calibration data and acquisition parameters are accessed, as shown in step 462, and a predetermined model is identified, as shown in step 471. Expected signal, noise, and signal-to-noise values are determined by utilizing the calibration data, acquisition parameters, and the predetermined model, as shown in step 472. These values may represent a prediction of signal, noise, and signal-to-noise values as a function of the calibration data, acquisition parameters, and the predetermined model. The expected signal, noise, and signal-to-noise values, and/or predictions, are provided to selection step 474, via line 482.

The selection step 474 may select the acquisition data, the global image analysis data, the local image analysis data, and/or the calibration/model data, or any combination thereof. That is, selection step 474 may select data received via lines 476, 478, 480, and/or 482, in any appropriate combination. The output from the selection step 474 is used to direct image processing as shown in step 484. That is, one or more of the acquisition data, the global image analysis data, the local image analysis data, and/or the calibration/model data are used to establish image processing parameters as described above. The processing performed in step 484 utilizes one or more of the inputs to generate processed data. The processed data may be stored, displayed, or transmitted to another location, as shown in step 488. The process ends, as shown in step 490.

Figure 5:
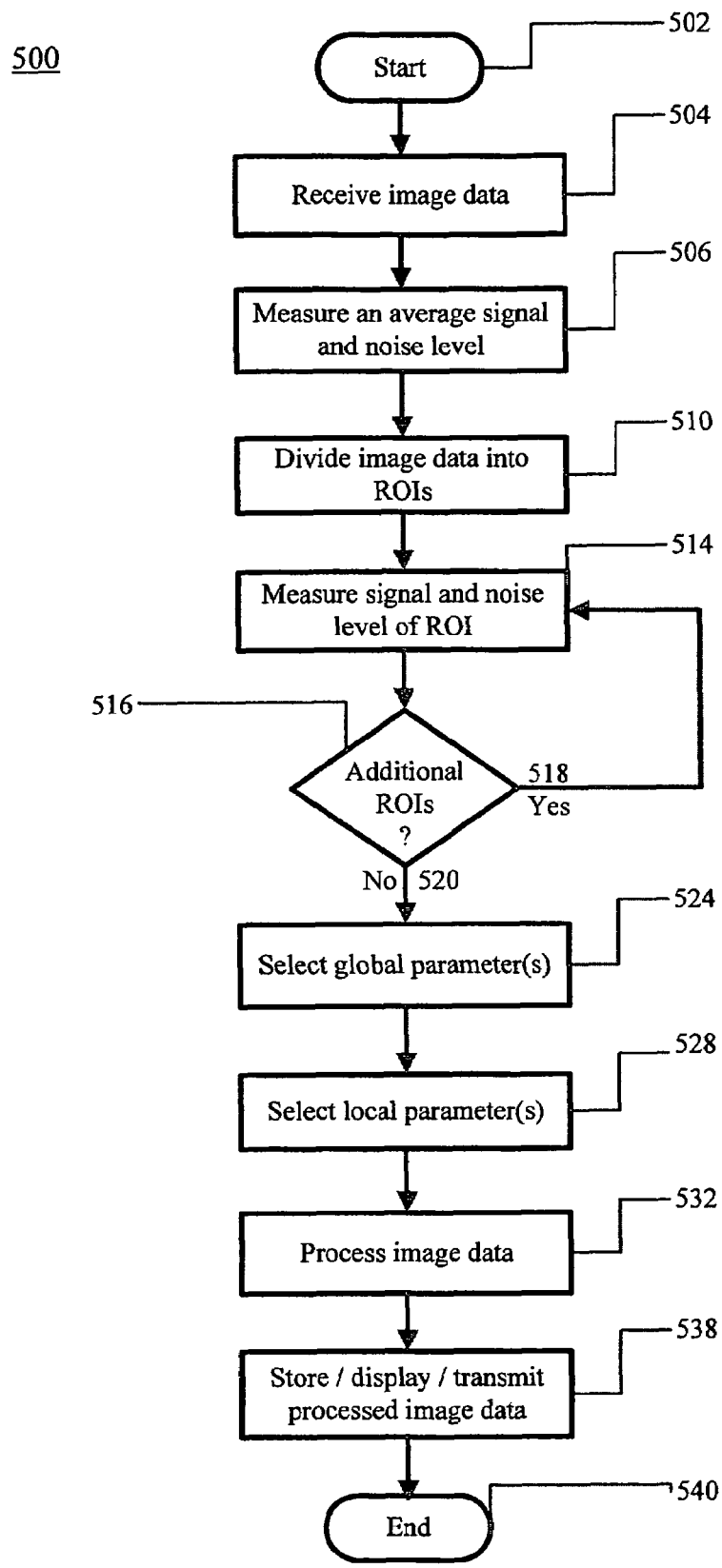
FIG. 5 is a flowchart of steps to implement another embodiment of the present invention.

FIG. 5 shows an algorithm 500 to generate output data from raw image data. The steps of FIG. 5 may be stored on a computer-readable medium, such as ROM, RAM, EEPROM, CD, DVD, or other non-volatile memory. Algorithm 500 may be retrieved, accessed, or downloaded from a remote location. Step 502 shows that the process begins.

Image data is received, as shown in step 504. This image data may have been subject to detector-specific processing. An average signal level and an average noise level are measured for the image data, as shown in step 506. The image data is divided into regions of interest (ROIs), as shown in step 510; Local signal and noise values for each ROI are measured, as shown in step 514. Decision step 516 determines whether there are additional ROIs. If so, "yes" line 518 leads back to step 514. If there are no any additional ROIs, "no" line 520 leads to step 524, which shows that global parameter(s) are selected based on the average signal level and the average noise level measured in step 506. Next, local parameter(s) for each ROI are selected based on the local signal and noise values for each ROI, as shown in step 528. The image data is processed, utilizing the global and local parameters, as shown in step 532. The processed data may be stored, transmitted, and/or displayed, as shown in step 538. End step 540 show the process ends.

It will be appreciated from the above that the invention may be implemented as computer software, which may be supplied on a storage medium or via a transmission medium, such as a local-area network or a wide-area network, such as the Internet.

Although illustrative embodiments of the invention have been described in detail herein with reference to the accompanying drawings, it is to be understood that the invention is not limited to those precise embodiments, and that various changes and modifications can be effected therein by one skilled in the art without departing from the scope and spirit of the invention as defined by the appended claims.

What is claimed is:

1. A method for establishing image processing parameters, comprising:
   accessing acquisition parameters for image data;
   identifying one or more regions of the image data;
   determining a signal level of each region;
   determining a noise level of each region;
   determining global image processing parameters as a function of the acquisition parameters; and
   establishing image processing parameters as a function of the acquisition parameters,
   wherein the acquisition parameters comprise one or more of an x-ray tube voltage, a pre-filtration, a focal spot size, an x-ray source to detector distance (SID), and a detector readout mode.

2. The method according to claim 1, further comprising:
   determining a signal level of the image data;
   determining a noise level of the image data; and
   establishing image processing parameters as a function of the acquisition parameters and the signal level and the noise level of the image data.

3. The method according to claim 1, further comprising:
   determining local image processing parameters for an individual region as a function of the signal level and the noise level of said individual region.

4. The method according to claim 1, further comprising:
   accessing calibration data; and
   identifying an expected signal level of the image data as a function of a predetermined model of the acquisition parameters and the calibration data;
   identifying an expected noise level of the image data as a function of a predetermined model of the acquisition parameters and the calibration data,
   wherein the expected signal level and the expected noise level are utilized in the step of establishing image processing parameters.

5. A method for identifying image processing parameters, comprising:
   accessing image data;
   accessing acquisition parameters for the image data;
   determining an average signal level and an average noise level of the image data;
   determining an average noise level of the image data;
   identifying one or more of regions of the image data;
   determining a signal level and a noise level of each region;
   identifying one or more global image processing parameters as a function of the acquisition parameters and the average signal level and the average noise level of the image data; and identifying one or more local image processing parameters for each region as a function of the signal level and the noise level of each region.

6. The method according to claim 5, wherein the acquisition parameters comprise one or more of an x-ray tube voltage and a detector readout mode.

7. The method according to claim 6, wherein the detector readout mode comprises one or more of a zoom size and a binning size.

8. The method according to claim 5, wherein the global image processing parameters comprise one or more of a kernel size and a gain of a dynamic range compression algorithm.

9. The method according to claim 5, wherein the local image processing parameters comprise one or more of a kernel size and a gain of an edge enhancement algorithm.

10. The method according to claim 5, further comprising:
accessing calibration data; and
identifying an expected signal level and an expected noise level of the image data as a function of a predetermined model of the acquisition parameters and the calibration data,
wherein the expected signal level and the expected noise level are utilized in the step of identifying global image processing parameters.

11. A method for selecting image processing parameters, comprising:
receiving image data;
measuring an average signal level and an average noise level of the image data;
dividing the image data into a plurality of regions of interest;
measuring a signal level and a noise level of each region of interest;
selecting global image processing parameters as a function of the average signal level and the average noise level of the image data; and
selecting local image processing parameters for each region of interest as a function of the signal level and the noise level of each region.

12. An apparatus for establishing image processing parameters, comprising:
means for accessing acquisition parameters for image data;
means for identifying one or more regions of the image data;
means for determining a signal level and a noise level of each region;
means for determining local image processing parameters for an individual region as a function of the signal level and the noise level of said individual region; and
means for establishing image processing parameters as a function of the acquisition parameters,
wherein the acquisition parameters comprise one or more of an x-ray tube voltage, a pre-filtration, a focal spot size, an x-ray source to detector distance (SID), and a detector readout mode.

13. The apparatus according to claim 12, further comprising:
means for determining a signal level and a noise level of the image data; and
means for establishing image processing parameters as a function of the acquisition parameters and the signal level and the noise level of the image data.

14. The apparatus according to claim 12, further comprising:
means for determining global image processing parameters as a function of the acquisition parameters.

15. The apparatus according to claim 12, further comprising:
means for accessing calibration data; and
means for identifying an expected signal level and an expected noise level of the image data as a function of a predetermined model of the acquisition parameters and the calibration data.

16. An apparatus for identifying image processing parameters, comprising:
means for accessing image data;
means for accessing acquisition parameters for the image data;
means for determining an average signal level and an average noise level of the image data;
means for identifying one or more of regions of the image data;
means for determining a signal level and a noise level of each region;
means for identifying one or more global image processing parameters as a function of the acquisition parameters and the average signal level and the average noise level of the image data; and
means for identifying one or more local image processing parameters for each region as a function of the signal level and the noise level of each region.

17. The apparatus according to claim 16, wherein the acquisition parameters comprise one or more of an x-ray tube voltage and a detector readout mode.

18. The apparatus according to claim 17, wherein the detector readout mode comprises one or more of a zoom size and a binning size.

19. The apparatus according to claim 16, wherein said global image processing parameters comprise one or more of a kernel size and a gain of a dynamic range compression algorithm.

20. The apparatus according to claim 16, wherein said local image processing parameters comprise one or more of a kernel size and a gain of an edge enhancement algorithm.

21. The apparatus according to claim 16, further comprising:
means for accessing calibration data; and
means for identifying an expected signal level and an expected noise level of the image data as a function of a predetermined model of the acquisition parameters and the calibration data.

22. An apparatus for selecting image processing parameters, comprising:
means for receiving image data;
means for measuring an average signal level and an average noise level of the image data;
means for dividing the image data into a plurality of regions of interest;
means for measuring a signal level and a noise level of each region of interest;
means for selecting global image processing parameters as a function of the average signal level and the average noise level of the image data; and
means for selecting local image processing parameters for each region of interest as a function of the signal level and the noise level of each region.

23. A system for establishing image processing parameters, comprising:
at least one memory;
at least one processor, coupled to the at least one memory, the at least one processor adapted to execute code that performs the steps of:
accessing acquisition parameters for image data; and establishing image processing parameters as a function of the acquisition parameters,
wherein said acquisition parameters comprise one or more of an x-ray tube voltage, a pre-filtration, a focal spot size, an x-ray source to detector distance (SID), and a detector readout mode; and program code for:
identifying one or more regions of the image data;
determining a signal level and a noise level of each region;
determining global image processing parameters as a function of the acquisition parameters; and
determining local image processing parameters for individual regions as a function of the signal level and the noise level of corresponding individual regions.

24. The system according to claim 23, further comprising program code for:
determining a signal level and a noise level of the image data; and
establishing image processing parameters as a function of the acquisition parameters and the signal level and the noise level of the image data.

25. The system according to claim 23, further comprising program code for:
accessing calibration data; and
identifying an expected signal level and an expected noise level of the image data as a function of a predetermined model of the acquisition parameters and the calibration data.

26. A system for identifying image processing parameters, comprising:
at least one memory;
at least one processor, coupled to the at least one memory, the at least one processor adapted to execute code that performs the steps of:
accessing image data;
accessing acquisition parameters for the image data;
determining an average signal level and an average noise level of the image data;
identifying one or more of regions of the image data;
determining a signal level and a noise level of each region;
identifying one or more global image processing parameters as a function of the acquisition parameters and the average signal level and the average noise level of the image data; and
identifying one or more local image processing parameters for each region as a function of the signal level and the noise level of each region.

27. The system according to claim 26, further comprising program code for:
accessing calibration data; and
identifying an expected signal level and an expected noise level of the image data as a function of a predetermined model of the acquisition parameters and the calibration data.

28. A system for selecting image processing parameters, comprising:
at least one memory;
at least one processor, coupled to the at least one memory, the at least one processor adapted to execute code that performs the steps of:
receiving image data;
measuring an average signal level and an average noise level of the image data;
dividing the image data into a plurality of regions of interest;
measuring a signal level and a noise level of each region of interest;
selecting global image processing parameters as a function of the average signal level and the average noise level of the image data; and
selecting local image processing parameters for each region of interest as a function of the signal level and the noise level of each region.

* * * * *